United States Patent
Sarnago Andía et al.

(10) Patent No.: US 10,673,347 B2
(45) Date of Patent: Jun. 2, 2020

(54) ELECTRONIC SYSTEM HAVING VARIABLE MODULAR POWER FOR GENERATING ELECTRICAL PULSES AND ASSOCIATED USES

(71) Applicants: UNIVERSIDAD DE ZARAGOZA, Saragossa (ES); UNIVERSITAT POMPEU FABRA, Barcelona (ES)

(72) Inventors: Hector Sarnago Andía, Saragossa (ES); Óscar Lucía Gil, Saragossa (ES); José Miguel Burdío Pinilla, Saragossa (ES); Alejandro Naval Pallarés, Saragossa (ES); Antoni Ivorra Cano, Barcelona (ES); Quim Castellví Fernández, Barcelona (ES)

(73) Assignees: UNIVERSIDAD DE ZARAGOZA, Saragossa (ES); UNIVERSITAT POMPEU FABRA, Barcelona (ES)

( * ) Notice: Subject to any disclaimer, the term of this patent is extended or adjusted under 35 U.S.C. 154(b) by 42 days.

(21) Appl. No.: 16/065,292

(22) PCT Filed: Dec. 22, 2016

(86) PCT No.: PCT/ES2016/070926
§ 371 (c)(1),
(2) Date: Jan. 18, 2019

(87) PCT Pub. No.: WO2017/109261
PCT Pub. Date: Jun. 29, 2017

(65) Prior Publication Data
US 2019/0126037 A1    May 2, 2019

(30) Foreign Application Priority Data
Dec. 22, 2015   (ES) .................... 201531870

(51) Int. Cl.
*H02M 7/00*  (2006.01)
*H02J 7/00*  (2006.01)
(Continued)

(52) U.S. Cl.
CPC ............... *H02M 7/00* (2013.01); *H02J 3/38* (2013.01); *H02J 7/0068* (2013.01);
(Continued)

(58) Field of Classification Search
CPC ............. A61N 1/327; A61B 18/1206; A61B 2018/00577; A61B 2018/0075;
(Continued)

(56) References Cited

U.S. PATENT DOCUMENTS 6,939,347 B2 * 9/2005 Thompson ......... A61B 18/1206
128/898
9,124,182 B2 * 9/2015 Chen ................. H02M 3/33507
(Continued)

FOREIGN PATENT DOCUMENTS

WO    2011/017802 A1    2/2011

OTHER PUBLICATIONS

Bae et al., "High-Power Pulse Generator With Flexible Output Pattern," *IEEE Transactions on Power Electronics* 25(7):1675-1684, Jul. 2010.
(Continued)

*Primary Examiner* — Emily P Pham
(74) *Attorney, Agent, or Firm* — Seed Intellectual Property Law Group LLP

(57) ABSTRACT

The disclosure relates to variable power modular electronic systems for generating unipolar and bipolar electrical pulses and associated uses thereof. In an embodiment, such a system includes one or more pulse generators for generating electrical pulses that can be connected in series; a charging circuit for charging the pulse generators; and a controller
(Continued)

communicatively coupled to the pulse generators and the charging circuit. Advantageously, each pulse generator may include an AC/DC rectifier and a DC/AC inverter connected to said AC/DC rectifier in a bridge configuration to generate bipolar output electrical pulses or pulse trains. In addition, the charging circuit may include a DC/DC step-up converter connected to an indirect DC/AC inverter. The system provided in various embodiments of the disclosure also provides a great versatility for adaptation to various applications and high output voltage and current values.

19 Claims, 1 Drawing Sheet

(51) Int. Cl.
| | |
|---|---|
| *H02J 3/38* | (2006.01) |
| *H02M 7/48* | (2007.01) |
| *A61N 1/32* | (2006.01) |
| *H02M 1/00* | (2006.01) |
| *A23L 3/32* | (2006.01) |
| *A61B 18/12* | (2006.01) |
| *A61B 18/00* | (2006.01) |

(52) U.S. Cl.
CPC ....... *H02M 7/4807* (2013.01); *H02M 7/4826* (2013.01); *A23L 3/32* (2013.01); *A23V 2002/00* (2013.01); *A61B 18/1206* (2013.01); *A61B 2018/0075* (2013.01); *A61B 2018/00577* (2013.01); *A61B 2018/1226* (2013.01); *A61B 2018/1266* (2013.01); *A61N 1/32* (2013.01); *A61N 1/327* (2013.01); *H02J 2207/20* (2020.01); *H02M 2001/007* (2013.01)

(58) Field of Classification Search
CPC .... A61B 2018/1226; A61B 2018/1266; A23L 3/32; A23V 2002/00; H02M 7/4807; H02M 7/4826; H02M 7/00; H02M 2001/007; H02J 3/38; H02J 7/0068; H02J 2207/20
See application file for complete search history.

(56) References Cited

U.S. PATENT DOCUMENTS

| | | | | |
|---|---|---|---|---|
| 2004/0076028 | A1* | 4/2004 | Achleitner | H02M 7/4807 363/65 |
| 2005/0190586 | A1* | 9/2005 | Radzinski | H02M 1/36 363/56.01 |
| 2008/0055941 | A1* | 3/2008 | Victor | H02M 3/158 363/17 |
| 2008/0266919 | A1* | 10/2008 | Mallwitz | H02M 3/158 363/124 |
| 2009/0052214 | A1* | 2/2009 | Edo | H01F 27/2804 363/123 |
| 2010/0309702 | A1* | 12/2010 | Yuan | H02M 7/4807 363/131 |
| 2011/0175579 | A1* | 7/2011 | Mazumdar | E02F 3/304 320/167 |
| 2012/0239026 | A1* | 9/2012 | Orszulak | A61B 18/1206 606/35 |
| 2012/0281441 | A1* | 11/2012 | Liu | H02M 7/48 363/35 |
| 2015/0230864 | A1* | 8/2015 | Xuan | A61B 18/22 606/2.5 |
| 2016/0329875 | A1* | 11/2016 | Song | H03H 1/0007 |
| 2017/0080222 | A1* | 3/2017 | Hayakawa | A61N 1/30 |
| 2018/0154142 | A1* | 6/2018 | Guo | A61N 1/36002 |

OTHER PUBLICATIONS

Bernal et al., "A Review of Pulse Generation Topologies for Clinical Electroporation," IECON 2015—41$^{st}$ Annual Conference of the IEEE Industrial Electronics Society, Nov. 9-12, 2015, pp. 000625-000630.

International Search Report dated Mar. 28, 2017, for International Application No. PCT/ES2016/070926, 2 pages.

Redondo et al., "Analysis of a modular generator for high-voltage, high-frequency pulsed applications, using low voltage semiconductors (<1 kV) and series connected step-up (1:10) transformers," *Review of Scientific Instruments* 78, 034702, 2007, 8 pages.

Varma et al., "Development of a Solid State Versatile Pulsar for High Voltage and High Power Applications," IEEE Pulsed Power Conference, 2009, pp. 1312-1316.

* cited by examiner

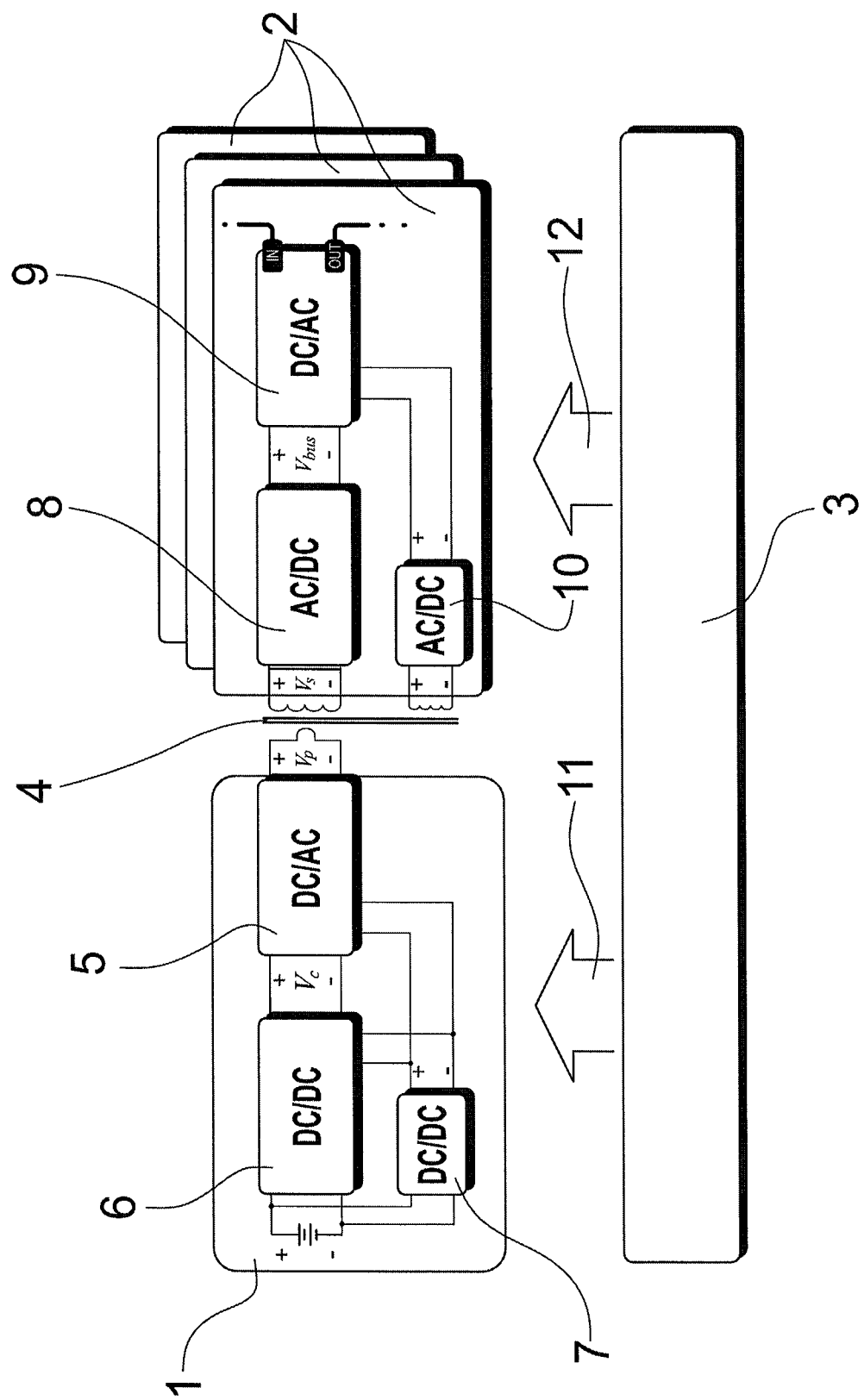

ELECTRONIC SYSTEM HAVING VARIABLE MODULAR POWER FOR GENERATING ELECTRICAL PULSES AND ASSOCIATED USES

BACKGROUND

Technical Field

The present disclosure relates to the technical field of electroporation devices used in medical treatments to improve absorption of medicines or destruction of tumor cells. More specifically, the disclosure relates to a modular electronic system with variable power for generating unipolar and bipolar electrical pulses. The field of greatest interest in the disclosure is biomedicine, although it is also applicable in other fields, such as for sterilization in the food industry.

Description of the Related Art

Electroporation is a technique used in medicine which involves applying a pulsed electric field to a living organism such that changes at a cell membrane level are triggered, which can be permanent or temporary depending on the strength of the applied field.

These electrical pulses are produced by generators with various characteristics depending on the desired electroporation technique or problem to treat. When the voltage across a plasma membrane exceeds the dielectric strength thereof, pores are formed which can close after some time. If the pore openings are temporary and reversible it is possible to introduce extracellular compounds in the cell interior for therapeutic purposes. Alternatively, the pores can remain open irreversibly, resulting in cell death by apoptosis. In this context the reversibility of the technique and the size and duration of the pores depend on the strength of the electric field applied and the exposure time of the cell to the same.

Irreversible electroporation (IRE) is a non-thermal ablation technique that is currently of great interest in the treatment of certain highly resistant tumors. It consists in applying strong electric fields to open tissue cell membranes and cause cell death. Some advantages of this technique over traditional tumors ablation techniques are the possibility of treating areas near major vessels, as these are not affected by thermal cooling, or the preservation of connective tissue, vessels and other ducts. To achieve irreversibility in the electroporation technique the generator must reach high voltages and currents, with a threshold that depends on the type of cells to be treated.

Currently available unipolar pulse generators for medical applications have insufficient maximum voltage levels for an efficient generalized use in electroporation techniques. This is the case for example with the system disclosed in Review of Scientific Instruments 78, 034702 (2007), in the article "Analysis of a modular generator for high-voltage, high-frequency pulsed applications, using low voltage semiconductors (1 kV) and series connected step-up (1:10) transformers" (L. M. Redondo et al.), which describes a modular generator that produces unipolar pulses that despite having a high voltage fall short of the voltage levels required for the applications considered herein. A similar case is the system disclosed in patent application WO 2011/017802 A1 (S. Jayaram et al.), which describes an electrical generator with a plurality of modules connected in cascade, and which generates unipolar pulses with variable output voltages depending on the number of modules included in the system.

In this way, although known modular generators allow solving some of the drawbacks of traditional techniques, there is a limit to the maximum voltages and currents attainable, and present several restrictions regarding the duration and configurability of the pulses generated, hindering their use in the field of irreversible electroporation of tumor cells.

In addition, existing generators used in irreversible electroporation that can provide the necessary output voltages and currents are however not too versatile, providing a limited range of voltages and limiting their use to certain specific types of cell or situations.

In view of the above, there is a need in the technical field for alternatives that allow solving the issues described above, reaching output voltage and current values suitable for a generalized use in irreversible electroporation, while providing devices that can be adapted for use in a large variety of situations or medical applications.

BRIEF SUMMARY

In various embodiments, the present disclosure provides a pulse generator technology based on a module structure and unipolar or bipolar pulses providing greater versatility and higher output voltage that generators of the prior art. In some embodiments, a high-voltage generator is provided based on a modular, versatile electronic system for power generation that comprises a control unit and allows adapting the strength and other characteristics of the electrical pulses to each specific application according to the number of modules used. Said generator may be preferably used in electroporation, and can be adapted to various specific problems or organs due to the versatility of the modular system and the possibility of attaining high voltages and currents.

The present disclosure provides, in one or more embodiments, a system comprising:

One or more electrical pulse generation modules, where said modules can be connected in series or in parallel. In connection in series, the output voltage of the pulses is the sum of the individual output voltages of each module. In connection in parallel, the total current is the sum of the currents of each module.

A charging unit for the generation modules.

A control unit for the generation modules and the charging unit.

Advantageously, the generation modules are coupled by isolation transformers to the charging unit, where said charging unit is arranged as the primary side of the transformers and the generation modules are arranged as the secondary side of the transformers.

In addition, each generation module preferably comprises an AC/DC rectifier at the output of the corresponding transformer, and a DC/AC inverter connected to said AC/DC rectifier, configured as a bridge for generating output electrical pulses or pulse rains, and the charging unit comprises a DC/DC step up converter connected to an indirect DC/AC inverter, where said DC/AC inverter is connected to the input of the transformer primary side.

This allows both obtaining a higher voltage and current in the pulses due to their bipolar character, and adding modules in series and in parallel to the device architecture, which in turn provides a technical solution that increases the versatility of the devices. In addition, bipolar pulses are obtained in the present disclosure by the bridge configuration of the inverter inside each generation module.

More specifically, the generator of the disclosure allows obtaining pulses with high voltages (on the order of 10-15 kV peak to peak) and currents (400-600 A peak to peak), greatly exceeding those of currently available generators used in clinical applications, providing in medical applications more than twice the voltage and five times the current obtained by technologies available in the market. This means that the generator of the disclosure allows reaching ablation volumes much higher than those available at this time and that, since no low-frequency transformer is used, a more compact and lightweight solution is obtained than that provided by current generators.

In addition, the modular design proposed by the system of the disclosure allows using the number of modules required to reach the desired voltage for a given application. This increases versatility of the output voltage with unipolar or bipolar pulses or pulse trains with a fully configurable width (from 1 µs) and number of pulses. This configurability implies the following technical advantages:

Attenuating the effect of electrochemical reactions. These reactions are harmful to both the electrodes and organic tissues.

Elimination of hydrogen and oxygen bubble formation due to hydrolysis.

Lower neurostimulation leading to unwanted muscle activation.

Possibility of applying quick bursts of short pulses, significantly reducing the total time of treatment.

An additional advantage is that the system of the disclosure does not require the use of an output transformer. This means a key difference, as it allows obtaining much lower output impedance that is therefore less influenced by the load. This aspect has great importance in electroporation, as both the electrodes and the tissue to connect lead to a highly variable load. In this way the disclosure can always guarantee a square voltage form at the output.

In a embodiment of the disclosure, one or more pulse generator modules comprise an auxiliary AC/DC block powered by the output of the isolation transformer and also connected to the AC/DC rectifier and the DC/AC inverter, to generate a power supply voltage for the same. Analogously, the charging unit may include an auxiliary DC/DC block, connected to the DC/DC step-up converter and the indirect DC/AC inverter, to generate a power supply voltage for the same.

In another embodiment of the disclosure, the frequency of the indirect DC/AC inverter of the charging unit is 200 kHz or higher, and the insulation voltage of the transformers may be 15 kV or higher.

In another embodiment of the disclosure, the generator includes a control architecture based on a programmable logic device (FPGA) that allows a full current and future implementation of advanced synchronization functions with ECG, protections, treatment automation, etc. This provides a greater versatility and adaptation of the output voltage pulses with respect to the treatment to be performed.

The control unit of the system of the disclosure also allows programming the number of generator modules active while the pulses are applied. This allows changing quickly the magnitude of the applied pulses or pulse trains, thereby configuring the shape thereof (for example, pulses or pulse trains with ladder form can be applied). This is of interest, for example, in applications related to electroporation-assisted gene transfection (gene electrotransfer). In this field of application of electroporation it has been demonstrated that protocols consisting in a single short high-magnitude pulse followed by a longer low-magnitude pulse are more effective than protocols with two or more short high-magnitude pulses.

In another embodiment of the disclosure, the control unit comprises at least one connection to the generation modules and at least one connection to the charging unit, where these connections are insulated by optical fiber. This provides an improved insulation that increases the safety of use of the system.

In another embodiment of the disclosure, the generator is powered by batteries instead of by direct connection to the power grid as those currently used, thereby improving safety and insulation during the use thereof and simplifying the approval of the device and compliance with electromagnetic compatibility regulations.

In another embodiment of the disclosure, the generator comprises a wireless communication subsystem by WiFi connection to a computer that allows configuring several parameters such as polarity, amplitude, number of pulses in each burst, number of bursts and repetition frequency. This possibility of wireless control considerably increases the safety and convenience of use.

Various embodiments of the present disclosure relate to the associated uses of the system, which comprise applications for sterilization of food, waste treatment, contamination control, treatment of metals or semiconductors, molecular biology tests, and/or medical or cosmetic treatments. In some embodiments, the uses of the system related to molecular biology tests, medical and/or cosmetic treatments comprise electroporation applications.

BRIEF DESCRIPTION OF THE SEVERAL VIEWS OF THE DRAWINGS

FIG. 1 shows a block diagram of the versatile power electronic modular system of the disclosure according to one or more embodiments thereof.

DETAILED DESCRIPTION

A detailed description of the disclosure is provided below with reference to one or more embodiments thereof based on FIG. 1 of this document. Said embodiments are provided for purposes of illustrating the claimed disclosure and is not meant to limit the same.

As described in preceding sections, the high-voltage generator disclosed by the present disclosure is based on a versatile power modular electronic system that allows adapting the design to the required output voltage and characteristics of the pulses, according to the specific application or treatment to provide.

Said FIG. 1 shows the general block diagram for the modular electronic power system of the disclosure, where said system essentially comprises a charging unit (1), one or more pulse generation modules (2) with a rectifier-inverter configuration, and a control unit (3). The pulse generation modules (2) are connected to the charging unit (1) by magnetic coupling through an isolation transformer (4).

The charging unit (1) may include a high-frequency indirect DC/AC inverter (5) connected to a previous DC/DC step-up converter (6). The main purpose of said charging unit (1) is to charge each of the generator modules (2) at the required voltage with the isolation transformer (4) through which they are coupled. It should be noted that the coupling via the transformer (4) provides the required insulation (greater than 15 kV); moreover, due to the high operating frequency (typically 200 kHz), a compact implementation of the system is achieved.

In addition to the aforementioned elements, the charging unit (1) comprises an auxiliary DC/DC block (7) that provides a power supply voltage $V_{aux,p}$, to control the DC/AC inverter (5) and the DC/DC step-up converter (6).

In addition, the pulse generation modules (2), arranged in the secondary side of the system isolation transformer (4), are in charge of generating the output voltage applied during the electroporation treatment. Each module (2) may include an AC/DC rectifier (8) and a DC/AC inverter (9) based on a bridge configuration, in order to enable the generation of output voltage bipolar pulses at each module (2).

Analogously to the arrangement of elements of the charging unit (1), each pulse generation module (2) can comprise an AC/DC auxiliary block (10) that is also powered from the secondary side of the isolation transformer (4), in charge of generating the power supply voltages $V_{aux,s}$ of the AC/DC rectifier (8) and the DC/AC inverter (9).

The pulse generation modules (2) of the system of the disclosure can be connected to one another in series, providing an output voltage that is the sum of the voltages generated by each of the individual generation modules (2). Similarly, the modules can be connected in parallel such that the current delivered is the sum of the currents of each module. In this way the disclosure provides a variable power stage that can adapt to the needs of the treatment to be performed in order to generate the required voltages and currents.

As described above, the system of the disclosure also comprises a control unit (3) that controls the electronic power system comprised of the charging unit (1) and each of the pulse generation modules (2). The control signals of the generation modules (2) are emitted using a programmable logic device (FPGA) integrated in each control unit (3). It should be noted that the generation of control signals by FPGA increases the versatility and adaptability of the output voltage pulses to the treatment to be performed. This is not possible in current commercial systems, which have severe restrictions regarding the types of voltage pulses that can be generated.

As mentioned in preceding sections, the control unit (3) may be configured with a programming means for the number of active generation modules (2) of the system during the application of the pulses, thereby allowing to change quickly the magnitude of the pulses or pulse trains applied, configuring the shape thereof.

In addition, due to the strict insulation requirements imposed by use and safety regulations for electroporation devices, the control signals may be insulated by optic fibers (11, 12).

Finally, the system of the disclosure may communicate using wireless means, for example a WiFi network connected to a remote computer (not shown in FIG. 1) through which the polarity, amplitude, number of pulses in each burst, number of bursts and repetition frequency thereof are configured.

The system of the disclosure provides satisfactory results in both treatment of plant tissues and treatment of live animal tissues.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A variable power modular electronic system for generating unipolar or bipolar electrical pulses, comprising:
   two or more inter-connectable pulse generation modules electrically coupled to one another in parallel or in series, the two or more inter-connectable pulse generation modules, in use, generate the unipolar or bipolar electrical pulses such that when the two or more inter-connectable pulse generation modules are coupled to one another in series an output voltage is a sum of individual output voltages of each pulse generation module, and when the two or more inter-connectable pulse generation modules are coupled to one another in parallel a total current is a sum of current of each pulse generation module;
   a charging circuit which, in use, charges the two or more inter-connectable pulse generation modules;
   a controller communicatively coupled to the two or more inter-connectable pulse generation modules and the charging circuit; and
   a transformer which couples the two or more inter-connectable pulse generation modules to the charging circuit, said charging circuit being electrically coupled to a primary side of the transformer and the two or more inter-connectable pulse generation modules being electrically coupled to a secondary side of the transformer,
   wherein each of the two or more inter-connectable pulse generation modules includes an AC/DC rectifier electrically coupled to a respective output of the secondary side of the transformer, and to an input of a first DC/AC inverter having a bridge configuration electrically coupled to an output of said AC/DC rectifier, the first DC/AC inverter, in use, outputs the unipolar or bipolar electrical pulses, wherein the charging circuit includes a DC/AC inverter electrically coupled to the primary side of the transformer, and
   wherein the charging circuit, in use, is fed from a battery or from an electric mains, and
   wherein the controller is programmed to control, in use, activation and deactivation of the two or more inter-connectable pulse generation modules while generating the unipolar or bipolar electrical pulses, for varying a magnitude of the unipolar or bipolar electrical pulses.

2. The variable power modular electronic system according to claim 1, wherein the two or more inter-connectable pulse generation modules include an auxiliary AC/DC rectifier powered by an output of the secondary side of the transformer, the auxiliary AC/DC rectifier, in use, supplies a power supply voltage to the AC/DC rectifier and the first DC/AC inverter.

3. The variable power modular electronic system according to claim 1, wherein the charging circuit includes a DC/DC converter and an auxiliary DC/DC converter electrically coupled to the DC/DC converter and to the DC/AC inverter, the auxiliary DC/DC converter, in use, supplies a power supply voltage to the DC/DC converter and to the DC/AC inverter.

4. The variable power modular electronic system according to claim 1, wherein an operating frequency of the DC/AC inverter of the charging circuit is 200 kHz or higher.

5. The variable power modular electronic system according to claim 1, wherein an insulation voltage of the transformer is 15 kV or higher.

6. The variable power modular electronic system according to claim 1, wherein the controller includes at least one connection to the two or more inter-connectable pulse generation modules and at least one connection to the charging circuit, said connections being insulated by optical fibers.

7. The variable power modular electronic system according to claim 1, wherein the controller is configured with a programming of a number of active pulse generation modules of the variable power modular electronic system during application of the unipolar or bipolar electrical pulses.

8. The variable power modular electronic system according to claim 1, further comprising a power supply configured to power at least one of the charging circuit, the two or more inter-connectable pulse generation modules, or the controller.

9. The variable power modular electronic system according to claim 1, further comprising at least one subsystem for communication with a computer which, in use, is operable to configure one or more parameters of the unipolar or bipolar electrical pulses.

10. The variable power modular electronic system according to claim 9, wherein the at least one subsystem for communication with the computer comprises a wireless connection to the computer via WiFi.

11. The variable power modular electronic system according to claim 1, the variable power modular electronic system being configured for use in applications for food sterilization, waste treatment, contamination control, treatment of metals or semiconductors, molecular biology tests, medical treatments, or cosmetic treatments.

12. The variable power modular electronic system according to claim 11, wherein the variable power modular electronic system is configured for use in electroporation applications.

13. The variable power modular electronic system according to claim 2, wherein the charging circuit includes a DC/DC converter and an auxiliary DC/DC converter electrically coupled to the DC/DC converter and to the DC/AC inverter, the auxiliary DC/DC converter, in use, supplies a power supply voltage to the DC/DC converter and to the DC/AC inverter.

14. The variable power modular electronic system according to claim 1 wherein the controller comprises a field-programmable gate array (FPGA).

15. The variable power modular electronic system according to claim 8 wherein the power supply comprises one or more batteries.

16. The variable power modular electronic system according to claim 9 wherein the one or more parameters of the unipolar or bipolar electrical pulses includes at least one of a polarity, an amplitude, a number, or a repetition frequency of the unipolar or bipolar electrical pulses.

17. The variable power modular electronic system according to claim 1, wherein the charging circuit includes a DC/DC converter electrically coupled to an input of the DC/AC inverter, and wherein the DC/DC converter is connectable to the battery or to an AC/DC rectifier electrically coupled to an input of the DC/DC converter, wherein the AC/DC rectifier is connected to the electric mains.

18. The variable power modular electronic system according to claim 1, wherein the transformer is an isolation transformer.

19. The variable power modular electronic system according to claim 3, wherein the DC/DC converter is a step-up converter.

* * * * *